United States Patent [19]

Bellini et al.

[11] Patent Number: 4,604,406
[45] Date of Patent: Aug. 5, 1986

[54] N-[6-METHOXY-5-(PERFLUOROALKYL)-1-NAPHTHOLYL]-N-METHYLGLYCINES AND THEIR THIONAPHTHOYL ANALOGS

[75] Inventors: Francesco Bellini, Mt. Royal, Canada; Kazimir Sestanj, Rocky Hill, N.J.

[73] Assignee: Ayerst, McKenna & Harrison, Inc., Montreal, Canada

[21] Appl. No.: 672,015

[22] Filed: Nov. 16, 1984

[51] Int. Cl.$^4$ .................. A61K 31/19; A61K 31/195; C07C 103/84; C07C 153/063
[52] U.S. Cl. ................................. 514/562; 514/563; 562/427; 562/444
[58] Field of Search ................ 562/427, 444; 514/562, 514/563

[56] References Cited

U.S. PATENT DOCUMENTS

| 4,254,108 | 3/1981 | Sestanj | 514/4 |
| 4,254,109 | 3/1981 | Sestanj | 514/4 |
| 4,369,188 | 1/1983 | Sestanj | 514/411 |
| 4,391,816 | 7/1983 | Sestanj et al. | 514/423 |
| 4,391,825 | 7/1983 | Bellini et al. | 514/562 |
| 4,439,617 | 3/1984 | Sestanj et al. | 560/39 |
| 4,447,452 | 5/1984 | Sestanj | 514/567 |

OTHER PUBLICATIONS

Stedman's Medical Dictionary, 24th Ed., Williams and Wilkins, Baltimore, MD, 1982, pp. 234–235.

Primary Examiner—Natalie Trousof
Assistant Examiner—Patricia M. Scott

[57] ABSTRACT

Disclosed herein are new aldose reductase inhibitors of the formula

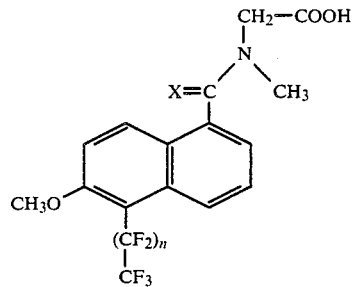

wherein n is an integer from 1 to 5 and X is a chalcogen, and methods of preparation. The derivatives are useful for treating or preventing diabetic complications.

8 Claims, No Drawings

N-[6-METHOXY-5-(PERFLUOROALKYL)-1-NAPH-THOLYL]-N-METHYLGLYCINES AND THEIR THIONAPHTHOYL ANALOGS

BACKGROUND OF THE INVENTION

This invention relates to N-[6-methoxy-5-(perfluoroalkyl)-1-naphthoyl]-N-methylglycines and their thionaphthoyl analogs, to processes for their preparation, to methods for using the derivatives, and to pharmaceutical preparations thereof. The derivatives have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators, see J. H. Kinoshita et al., Biochem. Biophys. Acta, 158,472 (1968) and references cited therein, have demonstrated that aldose reductase plays a central role in the etiology of glactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see. A. Pirie and R. van Heyningen, Exp. Eye Res., 3,124 (1964); L. T. Chylack and J. H. Kinoshita, Invest. Ophthal., 8,401 (1969) and J. D. Ward and R. W. R. Baker, Diabetol., 6,531 (1970).

1,3-Dioxo-1H-benz[de]isoquinoline-2(3H)-acetic acid has been reported to be an effective inhibitor of aldose reductase, see D. Dvornik et al., Science, 182,1146 (1973), and to be useful for the treatment of diabetic complications such as diabetic cataracts, neuropathy, nephropathy and retinopathy, see K. Sestanj, N. Simard-Duquesne and D. Dvornik, U.S. Pat. No. 3,821,383, June 28, 1974. Other compounds having a similar utility are the thioxo-1H-benz[de]isoquinoline-2(3H)-acetic acid derivatives of K. Sestanj, U.S. Pat. No. 4,254,108, Mar. 3, 1981 and 1H-benz[de]isoquinoline-2(3H)-acetic acid derivatives of K. Sestanj, U.S. Pat. No. 4,254,109, Mar. 3, 1981. Still other compounds having a similar utility are 2-thioxobenz[c,d]indole-1(2H)-acetic acid derivatives of K. Sestanj, U.S. Pat. No. 4,369,188, Jan. 18, 1983; N-naphthoylglycine derivatives of K. Sestanj et al., U.S. Pat. No. 4,439,617, Mar. 27, 1984; N-(naphthalenylthioxomethyl)amino acid derivatives of K. Sestanj et al., U.S. Pat. No. 4,391,816, July 5, 1983; N-[(2-naphthalenyl)thioxomethyl]glycine derivatives of K. Sestanj, U.S. Pat. No. 4,447,452, May 8, 1984; and N-[[6-(lower alkoxy)-5-(trifluoromethylthio)-1-naphthalenyl]thioxomethyl]-N-(lower alkyl)glycines of F. Bellini et al., U.S. Pat. No. 4,391,825, July 5, 1983. (S)-6-Fluoro-2,3-dihydrospiro(4H-1-benzopyran-4,4'-imidazolidine)-2',5'-dione (sorbinol) is still another compound that has received attention because of its aldose reductase inhibiting properties (see M. J. Peterson et al., Metabolism 28 (Suppl.1), 456 (1979). Accordingly, these compounds represent an important new approach for the treatment of diabetes mellitus.

The present application discloses novel perfluoroalkyl-1-naphthoyl-N-methylglycines and their thionaphthoyl analogs, represented below by formula I, which are effective inhibitors of aldose reductase. These are structurally different from the above noted aldose reductase inhibitors.

The closest of the previously reported compounds is seen in U.S. Pat. No. 4,439,617 (Example 52) and differs from the present derivatives by having different substituents, in that the compounds hereof have a perfluoroalkyl with 2–6 carbon atoms in the 5 position instead of the trifluromethyl of the above patent.

SUMMARY OF THE INVENTION

The N-[6-methoxy-5-(perfluoroalkyl)-1-naphthoyl]-N-methylglycines and their thionaphthoyl analogs of this invention are represented by formula I

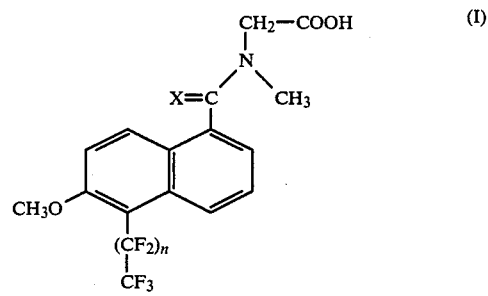

wherein n is an integer from 1 to 5 and X is a chalcogen.

A preferred group of the compounds of the invention is represented by formula I wherein n is 2.

The N-[6-methoxy-5-(perfluoroalkyl)-1-naphthoyl]-N-methylglycines and their thionaphthoyl analogs can be prepared by a process described hereinafter.

A method is provided for preventing or relieving diabetes mellitus associated complications in a diabetic mammal by administering to said mammal or prophylactic or alleviating amount of the compound of formula I. Such complications include neuropathy, nephropathy, retinopathy and cataracts.

The compounds of formula I, when admixed with a pharmaceutically acceptable carrier, form a pharmaceutical composition which can be used according to the preceding method.

DETAILED DESCRIPTION OF THE INVENTION

The compounds of this invention, represented by formula I, can exist in rotameric forms. More explicitly, mesomerism imparts a partial double bond character to the carbon-nitrogen bond of the amide and thioamide group. This partial double bond character leads to restricted rotation about the carbon nitrogen bond giving rise to cis and trans rotamers, the restricted rotation being augmented by the bulkiness of neighboring groups. Interconversion of the rotamers is possible and is dependent on the physical environment. As evidenced by its physical properties, the thermodynamically more stable rotamer exists exclusively in the crystalline state of the compound and is the predominant isomer present in equilabrated solutions. The less stable rotamer can be separated from the more stable rotamer by high performance liquid chromatography or by thin layer chromatography. The rotameric forms are included within the scope of this invention. For brevity, the compounds of this invention, including their rotameric forms, are referred to herein as compounds of formula I.

The term "chalcogen" as used herein is limited to oxygen and sulphur.

The term "organic proton acceptor" as used herein means the organic bases or amines, for instance, triethylamine, pyridine, N-ethylmorpholine and 1,5-diazabicyclo[4.3.0]non-5-ene.

The N-[6-methoxy-5-(perfluoroalkyl)-1-naphthoyl]-N-methylglycines and their thionaphthoyl analogs of this invention may be administered to mammals, for example, man, cattle or rabbits, either alone or in dosage forms, i.e., capsules or tablets, combined with pharmacologically acceptable excipients, see below.

Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the N-[6-methoxy-5-(perfluoroalkyl)-1-naphthoyl]-N-methylglycines and their thionaphthoyl analogs will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration, a 0.05–0.2% solution may be administered dropwise to the eye. The frequency of instillation varies with the subject under treatment from a drop every two or three days to once daily. For oral or parenteral adminstration a preferred level of dosages ranges from about 0.1 mg to about 200 mg per kilo of body weight per day, although aforementioned variations will occur. However, a dosage level that is in the range of from about 3.0 mg to about 30 mg per kilo of body weight per day is most satisfactory.

Unit dosage forms such as capsules, tablets, pills and the like may contain from about 5.0 mg to about 250 mg of the active ingredients of this invention with a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents for example, magnesium stearate.

The N-[6-methoxy-5-(perfluoroalkyl)-1-naphthoyl]-N-methylglycines and their thionaphthoyl analogs also can be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 36 ed., Medical Economics Co., Oradell, N.J., U.S.A., 1982. When used in combination, the N-[6-methoxy-5-(perfluoroalkyl)-1-naphthoyl]-N-methylglycines and their thionaphthoyl analogs are administered as described previously. The N-[6-methoxy-5-(perfluoroalkyl)-1-naphthoyl]-N-methylglycines and their thionaphthoyl analogs can be administered with the oral hypoglycemic agent in the form of a pharmaceutical composition comprising effective amounts of each agent.

The aldose reductase inhibiting property of the compounds of this invention and the utilization of the compounds in preventing, diminishing and alleviating diabetic complications are demonstrable in experiments using galactosemic rats, see Dvornik et at., cited above. Such experiments are exemplified hereinbelow after the listing of the following general comments pertaining to these experiments:

(a) Four or more groups of six male rates, 50–70 g, Sprague-Dawley strain, were used. The first group, the control group, was fed a mixture of laboratory chow (rodent laboratory chow, Purina) and glucose at 20% (w/w %) concentration. The untreated galactosemic group was fed a similar diet in which galactose is substituted for glucose. The third group was fed a diet prepared by mixing a given amount of the test compound with the galactose containing diet. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues were frozen and can be kept up to two weeks before being analyzed for dulcitol.

(c) The polyol determination was performed by a modification of the procedure of M. Kraml and L. Cosyns, Clin. Biochem., 2,373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was subtracted from the individual values found in the corresponding rat tissue to obtain the amount of polyol accumulated.]

The following tabulated results show that the N-[6-methoxy-5-(perfluoroalkyl)-1-naphthoyl]-N-methylglycines and their thionaphthoyl analogs of this invention diminish the accumulation of dulcitol in the lenses and sciatic nerves of rats fed galactose. The figures under L, N and D represent the percentage decrease of dulcitol accumulation in the tissues of the lens, sciatic nerve and diaphragm, respectively, for treated rats as compares to untreated rats.

Examination of the results tabulated below shows compound No. 7 at 11 mg/kg/day. The latter compound, which is also known as tolrestat, is presently undergoing clinical trials. Compound 4 as contrasted to tolrestat does not have sulfur in the molecule. This provides an opportunity to have a non-sulfur containing aldose reductase inhibitor. In a similar manner compound No. 3, N-[[5-(heptafluoropropyl-6-methoxy-1-naphthalenyl]thioxomethyl]-N-methylglycine, at 5 mg/kg/day, is superior to tolrestat at 4 mg/kg/day and approaches the activity of tolrestat at 11 mg/kg/day. Thus, compound No. 3 is about twice as active as tolrestat.

| # | Test compound | n | X | % inhibition in vitro $10^{-7}$ M | % lowering dulcitol accumulation in vivo | | | |
|---|---|---|---|---|---|---|---|---|
| | | | | | mg/kg/day | L | N | D |
| 1 | N—[[5-(Pentafluoroethyl)-6-methyoxy-1-naphthalenyl]-thioxomethyl]-N—methylglycine | 1 | S | 71 | 24.5 | 29 | 93 | 93 |
| 2 | N—[[5-(Pentafluoroethyl)-6-methoxy-1-naphthalenyl]-carbonyl]-N—methylglycine | 1 | O | 56 | 29 | 0 | 56 | 68 |
| 3 | N—[[5-(Heptafluoropropyl)-6-methoxy-1-naphthalenyl]thioxomethyl]-N—methylglycine | 2 | S | 75 | 5 | 20 | 52 | 76 |
| 4 | N—[[5-(Heptafluoropropyl)-6-methoxy-1-naphthalenyl]-carbonyl]-N—methylglycine | 2 | O | 63 | 10 | 19 | 45 | 38 |
| 5 | N—[[5-(Tridecafluorohexyl)-6-methoxy-1-naphthalenyl]-thioxomethyl]-N—methylglycine | 5 | S | 40 | 26 | 0 | 22 | 51 |
| 6 | N—[[5-(Tridecafluorohexyl)-6-methoxy-1-naphthalenyl]-carbonyl]-N—methylglycine | 5 | O | 47 | 25 | 0 | 0 | 0 |
| 7 | N—[[5-(Trifluoromethyl)-6-methoxy-1-naphthalenyl]-thioxomethyl]-N—methylglycine | 0 | S | 79 | 4 | 0 | 35 | 80 |
| | | | | | 11 | 14 | 86 | 89 |
| 8 | N—[[5-(Trifluoromethyl)-6-methoxy-1-naphthalenyl]-carbonyl]-N—methylglycine | 0 | 0 | 57 | 10 | 0 | 25 | 20 | that the prefluoroalkyls of this invention are surprisingly well suited as aldose reductase inhibitors. For example, compound No. 4, N-[[5-(heptafluoropropyl)-6-methoxy-1-naphthalenyl]carbonyl]-N-methylglycine at a dose of 10 mg/kg/day gives comparable results to

PROCESS

The N-[6-methoxy-5-(perfluoroalkyl)-1-naphthoyl]-N-methylglycines and their thionaphthoyl analogs can be prepared by the following reaction scheme:

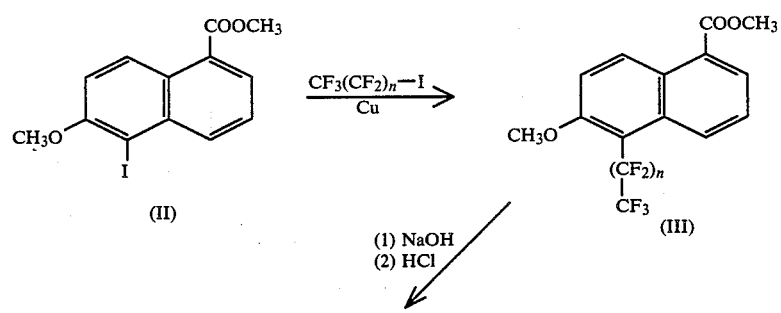

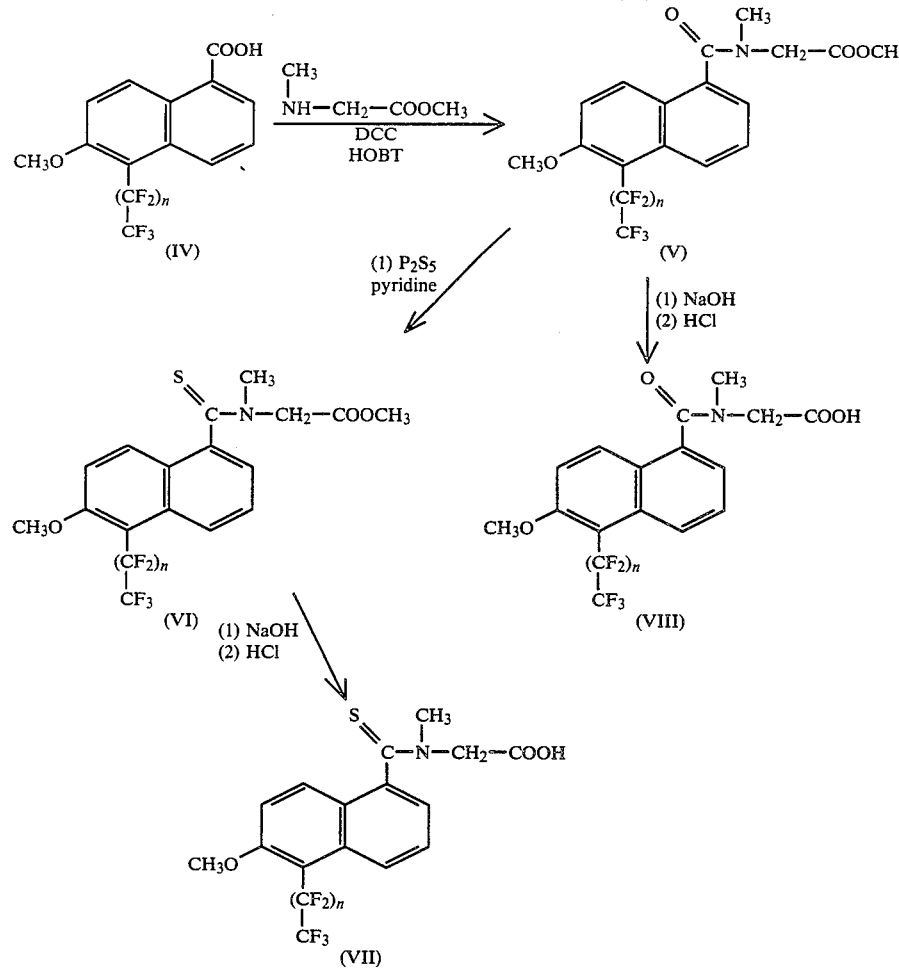

wherein perfluoroalkylating 6-methoxy-5-iodo-1-naphthalene carboxylic acid, methyl ester (II), a known compound, forms the corresponding perfluoroalkyl compound, (III), hydrolyzing said perfluoroalkyl compound to the corresponding carboxylic acid, (IV), coupling said acid with sarcosine methyl ester forms the corresponding substituted N-methylglycine, methyl ester, (V), hydrolyzing said substituted N-methylglycine, methyl ester forms the corresponding substituted N-methylglycine, (VIII). The N-methyl glycine, methyl ester, (V), can also be reacted with $P_2S_5$ to form the corresponding substituted thioxomethyl-N-methyl glycine, methyl ester, (VI), and hydrolyzing the latter forms the corresponding substituted thioxomethyl-N-methylglycine (VII).

EXAMPLE 1

N-[[6-Methoxy-5-(pentafluoroethyl)-1-naphthalenyl]-carbonyl]-N-methylglycine (VIII, n=1)

6-methoxy-5-iodo-1-naphthalene carboxylic acid, methyl ester (5 g, 0.0146 mol, Example 1F of U.S. Pat. No. 4,439,627), 1-iodo-pentafluoro-ethane (10.8 g, 0.0438 mol) activated copper powder (3 g), in a manner similar to Y. Kobayashi et al., J. Chem. Soc. Perkin I, 2755 (1980) and dry pyridine (45 ml) were heated in a pressure bottle to 120° C. for 20 hours. The mixture was cooled to room temperature, the precipitate filtered off, washed on the filter with ethyl acetate, and the filtrate washed with 2N hydrochloric acid, water, sodium bicarbonate, water and dried over anhydrous magnesium sulfate. The solvent was evaporated off, water and ethanol were added to the residue and the mixture left in a refrigerator. The product, 6-methoxy-5-(pentafluoroethyl)-1-naphthalenecarboxylic acid, methyl ester, was separated by filtration, washed with cold ethanol and dried (2.8 g). An additional amount (2 g) was obtained from the mother liquor. nmr (CDCl$_3$): $\delta$3.95 (s, 6H, OCH$_3$); $\delta$8.1 (m, 5H, H$_{ar}$) ms: m/e 334 (M$^+$), 303, 265, 234.

The 6-methoxy-5-(pentafluoroethyl)-1-naphthalenecarboxylic acid, methyl ester (2.82 g, 8.44 mmol), methanol (50 ml) and 2N aqueous sodium hydroxide (8.43 ml) were stirred at room temperature overnight. The mixture was cooled to 0° C., neutralized with 1N aqueous hydrochloric acid to pH 8 and the methanol evaporated off. Water was added to the residue and neutral impurities were removed by extraction with ethyl acetate. The aqueous layer was cooled to 0°, acidified to pH 1-3 with 1N aqueous hydrochloric acid, the product extracted with ethylacetate, the extract washed with brine and dried over anhydrous MgSO$_4$. Evaporation gave 2.14 g of crude 6-methoxy-5-(pentafluoroethyl)-1-naphthalene carboxylic acid which was used, without further purification, in the next step. nmr (DMSO): δ4.05 (s, 3H, OCH$_3$); δ8.0 (m, 4H, H$_{ar}$); δ9.1 (d, 1H, J=9, H$_{ar}$) ms: m/e 320 (M+), 303, 251, 203.

The crude 6-methoxy-5-(pentafluoroethyl)-1-naphthalene carboxylic acid (3.65 g, 11.4 mmol), 1-hydroxybenzotriazole (2.31 g, 17.1 mmol), dry distilled dimethylformamide (35 ml) and dicyclohexylcarbodiimide (2.82 g, 13.7 mmol) were stirred at room temperature for 1 hour. The mixture was cooled to 0° C., a solution of sarcosine methyl ester hydrochloride (3.18 g, 22.8 mmol) in dimethylformamide (30 ml) and N-ethyl morpholine (2.92 ml, 22.8 mmol) was added and stirring continued for 2 hours at room temperature. After cooling to 0° C., the precipitate (dicyclohexyl urea) was removed by filtration, the filtrate evaporated and the residue purified by HPLC (ethyl acetate/hexane 1:1, Waters Prep LC 500A). 1.5 g of pure, and 2.5 g of less pure N-[[6-methoxy-5-(pentafluoroethyl)-1-naphthalenyl]carbonyl]-N-methylglycine, methyl ester were obtained. nmr (DMSO): δ2.75 & 3.25 (2s, 3H, N—CH$_3$, rotamers); δ3.75 (s, 3H, OCH$_3$); δ3.97 (s, 3H, OCH$_3$); δ4.35 (broad, 2H, N—CH$_2$—CO); δ7.7 (m, 5H, H$_{ar}$). ms: m/e 405 (M+), 303, 195, 102.

To a solution of N-[[6-methoxy-5-(pentafluoroethyl)-1-naphthalenyl]carbonyl]-N-methylglycine, methyl ester (1.5 g, 3.7 mmol) in 2-methoxy-ethanol (30 ml) was added 2N aqueous sodium hydroxide (3.7 ml) at 0° C. under nitrogen atmosphere. Stirring was continued for 3 hours at room temperature. The reaction mixture was cooled to 0° C., neutralized (pH 8) with 1N aqueous hydrochloric acid, the solvent evaporated, the residue triturated with water, neutral material extracted with ethylacetate and the aqueous layer acidified to pH3 with 1N aqueous hydrochloric acid and the product extracted with ethyl acetate. The extract was washed with water, dried over anhydrous magnesium sulfate, the solvent evaporated off and the residue crystallized from ethyl acetate-hexane. Yield: 700 mg of the pure N-[[6-methoxy-5-(pentafluoroethyl)-1-naphthalenyl]-carbonyl]-N-methylglycine. An additional 170 mg were obtained from the mother liquor. Anal Calcd: C, 52.18% H, 3.61%, N, 3.58% Found: C, 52.31% H, 3.67% N, 3.58%. ir (nujol): 2500, 1900, 1725, 1580 cm$^{-1}$.uv, λmax(ε): 336 (3300), 324 (3000), 297 (5700), 285 (6200), 227 (53,400). nmr (DMSO): δ2.75 & 3.1 (2s, 3HN—CH$_3$, rotamers); δ3.85 & 4.2 (m, 2H, CH$_2$); δ4.0 (s, 3H, O—CH$_3$); δ7.7 (m, 5H, H$_{ar}$). ms: m/e 391 (M+), 346, 303.

EXAMPLE 2

N-[[6-methoxy-5-(pentafluoroethyl)-1-naphthalenyl]thioxomethyl]-N-methylglycine (VI, n=1)

Crude N-[[6-methoxy-5-(pentafluoroethyl)-1-naphthalenyl]carbonyl]-N-methylglycine, methyl ester, prepared as in Example 1 from 5.3 g or 13.4 mmol of 6-methoxy-5-(pentafluoroethyl)-1-naphthalene carboxylic acid, used without chromatrographic purification, was refluxed and stirred in dry pyridine (100 ml) with phosphorus pentasulfide (6 g) for 4 hours. After stirring overnight at room temperature, the mixture was hydrolyzed by addition of warm water, extracted with ethyl acetate, and the extract washed with 3N aqueous hydrochloric acid, water, sodium bicarbonate and brine. After drying and evaporation, the impure residue was dissolved in 25% ethyl acetate in hexane and the solution was filtered through silica gel. Evaporation of the filtrate and drying afforded 2.3 g. of fairly pure N-[[6-methoxy-5-(pentafluoroethyl)-1-naphthalenyl]thioxomethyl]-N-methylglycine, methyl ester. NMR: (CDCl$_3$): Compatible (mixture of rotamers). ms: m/e 421 (M+), 406, 388, 362, 319, 303.

The N-[[6-methoxy-5-(pentafluoroethyl)-1-naphthalenyl]thioxomethyl]-N-methylglycine, methyl ester (2.3 g, 5.46 mmol), 2-methoxyethanol (50 ml) and 2N aqueous sodium hydroxide (5.46 ml) were mixed at 0° C. and the mixture stirred at room temperature for 3 hours (until disappearance of the ester spot in t.l.c. with ethyl acetate/hexane 1:1). The mixture was cooled to 0° C., neutralized to pH 8 with 1N aqueous hydrochloric acid, evaporated, the residue triturated with water, the neutral material extracted with ethyl acetate and the aqueous layer acidified with 1N aqueous hydrochloric acid to pH3. The product was extracted with ethyl acetate, the extract washed with water, dried over anhydrous MgSO$_4$ and evaporated. The residue was purified by crystallization from chloroform/hexane to obtain 700 mg of the first crop and an additional 568 mg of the crude material from the mother liquor. Recrystallization of the first crop afforded 400 mg of the pure N-[[6-methoxy-5-(pentafluoroethyl)-1-naphthalenyl]thioxomethyl]-N-methylglycine. The recrystallization of mother liquor gave further 291 mg. mp. 164°-165° C. Anal. Calcd: C, 50.13% H, 3.46% N, 3.44% Found: C, 49.42%, H, 3.58% N, 3.40%. nmr (DMSO): δ2.95 (s, 3H, N—CH$_3$); δ3.97 (s, 3H, OCH$_3$); δ4.9 (q, 2H, CH$_2$); δ7.1-8.4 (m, 5H, H$_{ar}$). ir (nujol): 1700, 1723, 1750 cm$^{-1}$ uv, λmax(ε): 338 (3990), 269 (13,000), 227 (45,400) ms: m/e 407 (M+), 363, 319.

EXAMPLE 3

N-[[5-(Heptafluoropropyl)-6-methoxy-1-naphthalenyl]-carbonyl]-N-methylglycine (VIII, n=2)

The 6-methoxy-5-iodo-1-naphthalene carboxylic acid, methyl ester (5 g, 0.0146 mol), 1-iodo-heptafluoropropane (8.9 g, 4.35 ml, 0.03 mol), activated copper powder (2.8 g, 0.044 at) and dry distilled dimethylformamide (35 ml) were heated with stirring for 4 hours at 150° in a pressure bottle. The reaction mixture was cooled to room temperature, the solid removed by filtration and washed on the filter with ether. The filtrate was washed with water and dried over anhydrous magnesium sulfate. The solvent was evaporated and the residue left in a refrigerator to crystallize (5.6 g). A small amount of 5-(heptafluoropropyl)-6-methoxy-1-naphthalene carboxylic acid, methyl ester was recrystallized from ethanol. m.p. 74°-75° C. ms: m/e 384 (M+), 353, 265. nmr (CDCl$_3$): δ4.0 (s, 6H, OCH$_3$); δ8.25 (m, 5H, H$_{ar}$).

The 5-(heptafluoropropyl)-6-methoxy-1-naphthalene carboxylic acid, methyl ester (5.6 g, 0.0146 mol), methanol (40 ml) and 4N aqueous sodium hydroxide (7.3 ml) were stirred at room temperature for 30 minutes and then refluxed for 4 hours. After standing overnight, the mixture was cooled to 0° and neutralized with aqueous 1N hydrochloric acid. Methanol was evaporated, the residue triturated with water and the mixture acidified (pH ~3) with 1N aqueous hydrochloric acid. The pasty precipitate was extracted with ethyl acetate, the organic layer washed with water, dried over anhydrous magnesium sulfate and evaporated. The crude product, 5-(heptafluoropropyl)-6-methoxy-1-naphthalene carboxylic acid, (5.15 g) was used in the next step without further purification. One part of the product was recrystallized from chloroform-hexane for spectral identification. ms: m/e 370, 251, 203. nmr (CDCl$_3$): δ4.0 (s, 3H, OCH$_3$); δ7.4– 9.35 (m, 5H, H$_{ar}$); δ10.7 (b, 1H, COOH).

The crude acid (5.15 g, 0.0139 mol), 1-hydroxybenzotriazole (2.82 g, 0.021 mol), dry distilled dimethylformamide (40 ml) and dicyclohexylcarbodiimide (3.44 g, 0.0167 mol) were stirred for 1 hour at room temperature. A solution of sarcosine methyl ester hydrochloride (3.88 g, 0.0278 mol) in dimethylformamide (30 ml) was added to the above mixture followed by N-ethyl morpholine (3.55 ml). The reaction mixture was stirred overnight, the precipitate (dicyclohexyl urea) removed by filtration, the filtrate evaporated to dryness and the residue dissolved in ethyl acetate. The solution was washed with sodium bicarbonate and water, dried over anhydrous magnesium sulfate and evaporated. The residue was purified by chromatography using Waters Prep LC 500A instrument with ethyl acetate-hexane (1:1) system. Yield 3.3 g (a very pure fraction amounted to 1.5 g) N-[[5-(heptafluoropropyl)-6-methoxy-1-naphthalenyl]carbonyl]-N-methylglycine, methyl ester. ms: m/e 455, 353, 102. nmr (CDCl$_3$): δ2.85 (s, 3H, N—CH$_3$); δ3.4 (q, 2H, CH$_2$); δ3.82 (s, 3H, OCH$_3$); δ3.95 (s, 3H, OCH$_3$); δ7.2-8.4 (m, 5H, H$_{ar}$).

To a solution of the N-[[5-(heptafluoropropyl)-6-methoxy-1-naphthalenyl]carbonyl]-N-methylglycine, methyl ester (1.52 g, 3.34 mmol) in 2-methoxy-ethanol (20 ml) was added 2N aqueous sodium hydroxide (3.34 ml) at 0° C. under nitrogen atmosphere. Stirring was continued at room temperature for 2 hours. The mixture was cooled to 0° C., neutralized with 1N aqueous hydrochloric acid to pH7, the solvent evaporated, the residue dissolved in water and acidified to pH3. The product was isolated by filtration, washed with water and crystallized from chloroform-hexane giving 1.14 g of N-[[5-(heptafluoropropyl)-6-methoxy-1-naphthalenyl]carbonyl]-N-methylglycine. m.p. 195°–197° C. Anal. Calcd: C, 49.02% H, 3.20% N, 3.18%. Found: C, 48.29% H, 3.20% N, 3.11%. ir (nujol): 2500, 1900, 1725, 1580, 1220, 1120 cm$^{-1}$. uv, λmax(ε): 336 (3400), 324 (3120), 298 (5960), 286 (6310), 227 (52,600). nmr (DMSO): 67 2.75 (s, 3H, N—CH$_3$); δ3.98 (s, 3H, O—CH$_3$); δ4.1 (m, 2H, N—CH$_2$); δ7.75 (m, 5H, H$_{ar}$). ms: m/e 441 (M$^+$), 396, 353, 322, 69 also [442 (M+1)$^+$, 443 (M+2)$^+$.

EXAMPLE 4

N-[[5-heptafluoropropyl)-6-methoxy-1-naphthalenyl]-thioxomethyl]-N-methyl glycine (VI, n=2)

N-[[5-(Heptafluoropropyl)-6-methoxy-1-naphthalenyl]carbonyl]-N-methylglycine, methyl ester (1.78 g, 0.0039 mol), prepared as in Example 3, dry pyridine (30 ml) and phosphorus pentasulfide (2 g, 0.009 mol) were refluxed under nitrogen for 6 hours. The still warm mixture was poured into warm water, extracted with ethyl acetate, the extract washed with 3N aqueous hydrochloric acid, saturated sodium bicarbonate and brine. The solvent was evaporated, the oily residue was dissolved in hexane-ethyl acetate (3:1) mixture and the solution filtered through silica gel to remove some polar material. After evaporation of the solvent, the oily product N-[[5-(heptafluoropropyl)-6-methoxy-1-naphthalenyl]thioxomethyl]-N-methylglycine, methyl ester, solidified on scratching (1.07 g). m.p. 107°–109° C. ms: m/e 471 (M$^+$), 440, 412, 369, 207, 102. nmr (CDCl$_3$): δ3.0 (s, 3H, N—CH$_3$); δ3.85 (s, 3H, OCH$_3$); δ3.92 (s, 3H, OCH$_3$); δ4.93 (q, 2H, CH$_2$); δ7.1-8.4 (m, 5H, H$_{ar}$).

To a solution of the N-[[5-heptafluoropropyl)-6-methoxy-1-naphthalenyl]thioxomethyl]-N-methylglycine, methyl ester (1.07 g, 2.27 mmol) in 2-methoxy ethanol (15 ml) was added 2N aqueous sodium hydroxide (2.27 ml) at 0° C. under nitrogen atmosphere. The mixture was stirred at room temperature overnight, cooled to 0° C., neutralized (pH7-8) with aqueous 1N hydrochloric acid and evaporated to dryness. The residue was triturated with water, acidified to pH3 and the product extracted with ethyl acetate, the extract washed repeatedly with water, dried over anhydrous magnesium sulfate and the solvent evaporated. The oily residue crystallized from chloroform-hexane yielded 484 mg of N-[[5-(heptafluoropropyl)-6-methoxy-1-naphthalenyl]thioxomethyl]-N-methylglycine. m.p 162°–163° C. Anal. Calcd: C, 47.27%, H, 3.09% N, 3.06%. Found: C, 47.03% H, 3.08% N, 3.03%, ir (CHCl$_3$): 2950 (broad), 1722, 1760 (infl.), 1110 cm$^{-1}$ uv, λmax(ε): 338 (4210), 228 (48,350). nmr(CDCl$_3$): δ3.05 (s, 3H, N—CH$_3$); δ3.93 (s, 3H, O—CH$_3$); δ4.6 & 5.4 (2d, 2H, N—CH$_2$, J=17); δ7.6 (m, 5H, H$_{ar}$); δ8.9 (b, 1H, COOH). ms: m/e 457 (M$^+$), 456, 412, 338, 369, 207, 169, 69.

EXAMPLE 5

N-[[6-methoxy-5-(tridecafluorohexyl)-1-naphthalenyl]-N-methylglycine (VIII n=5)

The 6-methoxy-5-iodo-1-naphthylene carboxylic acid, methyl ester (10 g, 0.0292 mol), 1-iodo-tridecafluoro-hexane (26.05 g, 0.0584 mol), activated copper powder (5.6 g) and dry, distilled dimethylformamide (30 ml) were heated to 140° C. with stirring in a pressure bottle for 4 hours. The mixture was cooled, copper removed by filtration, the solvent evaporated, the residue dissolved in ethyl acetate and the solution washed with brine. Drying over anhydrous magnesium sulfate and evaporation, gave 15.6 g of the product, 6-methoxy-5-(tridecafluorohexyl)-1-naphthalene carboxylic acid methyl ester, which was used in the next step without further purification. A small amount (400 mg) was purified by column chromatography (SiO$_2$, hexane-ethyl acetate) for spectraal identification (429 mg of pure material). ms: m/e 534, 515, 503, 265, 119, 69. nmr (CDCl$_3$): δ4.05 (s, 6H, 2OCH$_3$); δ7.3–9.3 (m, 5H, H$_{ar}$).

To a solution of 6-methoxy-5-(tridecafluorohexyl)-1-naphthalene carboxylic acid methyl ester (0.919 g, 17.2 mmol) in methanol (10 ml) and 2-methoxy ethanol (3 ml) was added aqueous 4N sodium hydroxide (0.86 ml). The mixture was stirred at room temperature for 30 minutes and then refluxed for 2 hours. The solvent was evaporated, the residue triturated with water, the neutral material extracted with ethyl acetate and the aqueous layer separated and acidified with aqueous 1N hydrochloric acid to pH3. The product was extracted with ethyl acetate, the extract washed with water, dried over anhydrous magnesium sulfate and evaporated (745 mg). The product, 6-methoxy-5-(tridecafluorohexyl)-1-naphthalene carboxylic acid, was used in the next stage without further purification. ms: m/e 520 (M$^+$), 328, 251. nmr (DMSO): δ4.0 (s, 3H, OCH$_3$); δ7.5-8.5 (m, 4H, H$_{ar}$); δ9.2 (d, 1H, H$_{ar}$, J=10).

6-Methoxy-5-(tridecafluorohexyl)-1-naphthalene carboxylic acid (9.8 g, 0.0188 mol), 1-hydroxybenzotriazole (3.82 g, 0.0283 mol), dicyclohexylcarbodiimide (4.66 g, 0.0226 mol) and dry, distilled dimethylformamide (70 ml) were stirred at room temperature for 1 hour. A solution of sarcosine methyl ester hydrochloride (5.26 g, 0.0377 mol) in dimethylformamide (50 ml) and N-ethylmorpholine (4.82 ml) was added to the above reaction mixture. Stirring was continued for 3 hours. Dicyclohexylurea was removed by filtration, washed with dimethylformamide on the filter, the combined filtrates were evaporated and the residue dissolved in ethyl acetate. The solution was washed with 1N aqueous hydrochloric acid, water, saturated sodium bicarbonate, water and dried over anhydrous magnesium sulfate. Evaporation of the solvent gave 10 g of crude N-[[6-methoxy-5-(tridecafluorohexyl)-1-naphthalenyl]-carbonyl]-N-methylglycine, methyl ester, which was purified by chromatography by using Waters Prep LC 500A instrument with ethyl acetate-hexane (1:1) system. Yield: 5.15 g. ms: m/e 605 (M+), 503, 336, 206. nmr (DMSO): δ2.75 & 3.1 (2s, 3H, N—CHHd 3, rotamers); 3.5 & 3.75 (2s, 3H, O—CH₃, rotamers); δ4.0 (s, 3H, OCH₃) δ4.0–4.4 (b, 2H, CH₂); 7.2–8.4 (m, 5H, H$_{ar}$).

To a solution of N-[[6-methoxy-5-(tridecafluorohexyl)-1-naphthalenyl]carbonyl]-N-methylglycine, methyl ester (1.5 g, 2.48 mmol) in 2-methoxy-ethanol (20 ml) was added 4N aqueous sodium hydroxide (1.24 ml) at 0° C. under nitrogen atmosphere. Stirring was continued for 2 hours at room temperature. The reaction mixture was diluted with water, acidified with 1N aqueous hydrochloric acid to pH3 and extracted with ether. The extract was washed with water, dried over anhydrous magnesium sulfate and evaporated. The pure product N-[[6-methoxy-5-(tridecafluorohexyl)-1-naphthalenyl]-N-methylglycine (731 mg) was obtained by crystallization from ethanol-water. Additional product (492 mg) was isolated from the mother liquor. Anal. Calcd: C, 42.65% H, 2.39% N, 2.37%. Found: C, 42.48% H, 2.43% N, 2.42%. ir (nujol): 2500, 1700, 1600, 1580, 1500, 920 cm⁻¹. uv, λmax(ε): 337 (3490), 324 (3250), 297 (6150), 286 (6450), 227 (52,690). nmr (DMSO): δ2.75 & 3.13 (2s, 3H, N—CH₃, rotamers); δ4.00 (s, 3H, OCH₃); δ4.23 (b, 2H, CH₂); δ7.2–8.4 (m, 5H, H$_{ar}$); δ12.8 (b, 1H, NH+). ms: m/e 591 (M+), 573, 547, 504, 322.

EXAMPLE 6

N-[[6-Methoxy-5-(tridecafluorohexyl)-1-naphthalenyl]-thioxomethyl]-N-methylglycine (VI n=5)

N-[[6-methoxy-5-(tridecafluorohexyl)-1-naphthalenyl]carbonyl-N-methylglycine, methyl ester (100 mg, 0.165 mmol), prepared as in Example 5, phosphorus pentasulfide (67 mg) and dry pyridine (2 ml) were refluxed for 2 hours. After stirring overnight at room temperature, the mixture was refluxed for 2 additional hours, poured into water and extracted with ether. The ether extract was washed with 1N aqueous hydrochloric acid, water, saturated sodium bicarbonate and brine. After drying over anhydrous magnesium sulfate, the solvent was evaporated giving 92.8 mg of the crude N-[[6-methoxy-5-(tridecafluorohexyl)-1-naphthalenyl]-thioxomethyl]-N-methylglycine, methyl ester, which was used in the next preparation without further purification. ms: m/e 622 (M+H)+, 562, 519, 503, 352. nmr (CDCl₃): δ2.84 & 3.04 (2s, 3H, N—CH₃, rotamers); δ3.82 & 3.95 (2s, 3H, O—CH₃, rotamers) δ3.4 & 5.5 (2d, 2H, CH₂, J=17); δ7.3 (m, 3H, H$_{ar}$); δ8.2 (m, 2H, H$_{ar}$).

To a solution of N-[[6-methoxy-5-(tridecafluorohexyl)-1-naphthalenyl]thioxomethyl]-N-methylglycine, methyl ester (2.53 g, 4.07 mmol) in 2-methoxy-ethanol (20 ml) was added aqueous 4N sodium hydroxide (2 ml) with stirring under nitrogen atmosphere at 0° C. Stirring was continued for 2 hours at room temperature. The mixture was diluted with water, neutral material removed by extraction with ether, the aqueous layer acidified to pH3 and the product extracted with ether. The extract was washed with water and dried over anhydrous magnesium sulfate. Evaporation and trituration with hexane gave 818 mg of N-[[6-methoxy-5-(tridecafluorohexyl)-1-naphthalennyl]thioxomethyl]-N-methylglycine. m.p. 180° C. (dec.) Anal. Calcd: C, 41.53% H, 2.32% N, 2.31% Found: C, 39.79% H, 2.34% N, 2.29%. ms: m/e 607 (M+), 562, 519, 338. ir (CHCl₃): 3400, 1720, 1600, 1500, 1450, 1140, 920 cm⁻¹. uv, λmax(ε): 307 (4310) 272 (11,600), 228 (44,890). nmr (CDCl₃): ε2.90 (s, 3H, N—CH₃); δ3.94 (s, 3H, OCH₃); δ4.25 & 5.25 (2d, 2H, CH₂, J=16); δ7.2 (m, 1H, H$_{ar}$); δ7.55 (m, 2H, H$_{ar}$); δ7.9 (j, 1H, H$_{ar}$); δ8.55 (m, 1H, H$_{ar}$).

We claim:

1. A compound of formula I

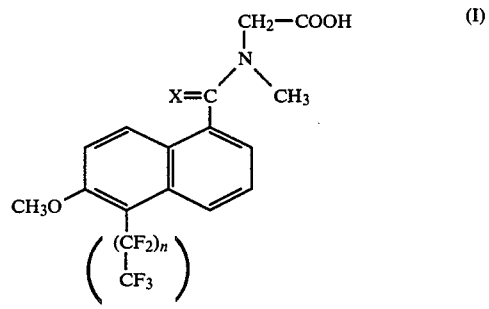

wherein n is an integer from 2 to 5 and X is oxygen or sulfur.

2. The compound of claim 1, wherein n is 2.

3. The compound of claim 2, which is [N-[[5 heptafluropropyl)-6-methoxy-1-naphthalenyl]thioxomethyl]-N-methyl glycine]N-[[5-(heptafluoropropyl)-6-methoxy-1-naphthalenyl]thioxomethyl]-N-methylglycine.

4. The compound of claim 2, which is N-[[5-(heptafluoropropyl)-6-methoxy-1-naphthalenyl]carbonyl]-N-methylglycine.

5. The compound of claim 1, which is N-[[6-methoxy-5-(tridecafluorohexyl)-1-naphthalenyl]thioxomethyl]-N-methylglycine.

6. The compound of claim 1, which is N-[[6-[M]methoxy-5-(tridecafluorohexyl)-1-naphthalenyl]carbonyl]-N-methylglycine.

7. A pharmaceutical composition for preventing or relieving neuropathy, nephropathy, retinopathy or cataracts in a diabetic mammal by inhibiting aldose reductase, which comprises an effective amount of a compound of claim 1 and a pharmaceutically acceptable carrier.

8. A method of preventing or relieving neuropathy, nephropathy, retinopathy or cataracts in a diabetic mammal by inhibiting aldose reductase, which comprises administering to said mammal an alleviating or prophylactic amount of a compound of claim 1.

* * * * *